United States Patent
McDermott et al.

[11] Patent Number: 5,231,865
[45] Date of Patent: Aug. 3, 1993

[54] DIFFUSION GAS DILUTER

[75] Inventors: Wayne T. McDermott, Allentown; Richard C. Ockovic, Northampton, both of Pa.

[73] Assignee: Air Products and Chemicals, Inc., Allentown, Pa.

[21] Appl. No.: 816,193

[22] Filed: Jan. 2, 1992

[51] Int. Cl.⁵ ............................................. G01N 15/10
[52] U.S. Cl. .................................. 73/28.04; 73/865.5
[58] Field of Search ............... 73/28.01, 863.11, 28.04, 73/865.5

[56] References Cited

U.S. PATENT DOCUMENTS

| | | | |
|---|---|---|---|
| 2,386,282 | 10/1945 | Watson et al. | 73/28.04 |
| 3,208,286 | 9/1965 | Richard | 73/865.5 |
| 3,494,217 | 2/1970 | Tanaka et al. | 73/865.5 |
| 3,680,388 | 8/1972 | Critchley et al. | 73/863.11 |
| 3,771,291 | 11/1973 | Klingler | 73/865.5 |
| 3,822,582 | 7/1974 | Etkin | 73/82.01 |
| 3,854,321 | 12/1974 | Dahneke | 73/28.01 |
| 3,954,428 | 5/1976 | Marple et al. | 73/28.01 |
| 4,338,029 | 7/1982 | Macourt | 73/28.01 |
| 4,463,595 | 8/1984 | Yeh et al. | 73/82.01 |
| 4,684,251 | 8/1987 | Brouwer et al. | 356/315 |
| 5,026,155 | 6/1991 | Ockovic et al. | 356/37 |
| 5,058,440 | 10/1991 | Graze, Jr. | 73/863.83 |

FOREIGN PATENT DOCUMENTS

| | | | |
|---|---|---|---|
| 0158137 | 1/1963 | U.S.S.R. | 73/28.04 |
| 0857791 | 8/1981 | U.S.S.R. | 73/28.04 |

*Primary Examiner*—Hezron E. Williams
*Assistant Examiner*—George Dombroske
*Attorney, Agent, or Firm*—Geoffrey L. Chase; James C. Simmons; William F. Marsh

[57] ABSTRACT

A diffusion diluter is described and a method for using such apparatus with a condensation nucleus counter, wherein a particle containing reactive gas is diluted with an inert diluent gas to diminish the reactive character of the particle-containing gas without disturbing the particle concentration of the gas allowing it to be accurately and safely measured for its particle content.

22 Claims, 3 Drawing Sheets

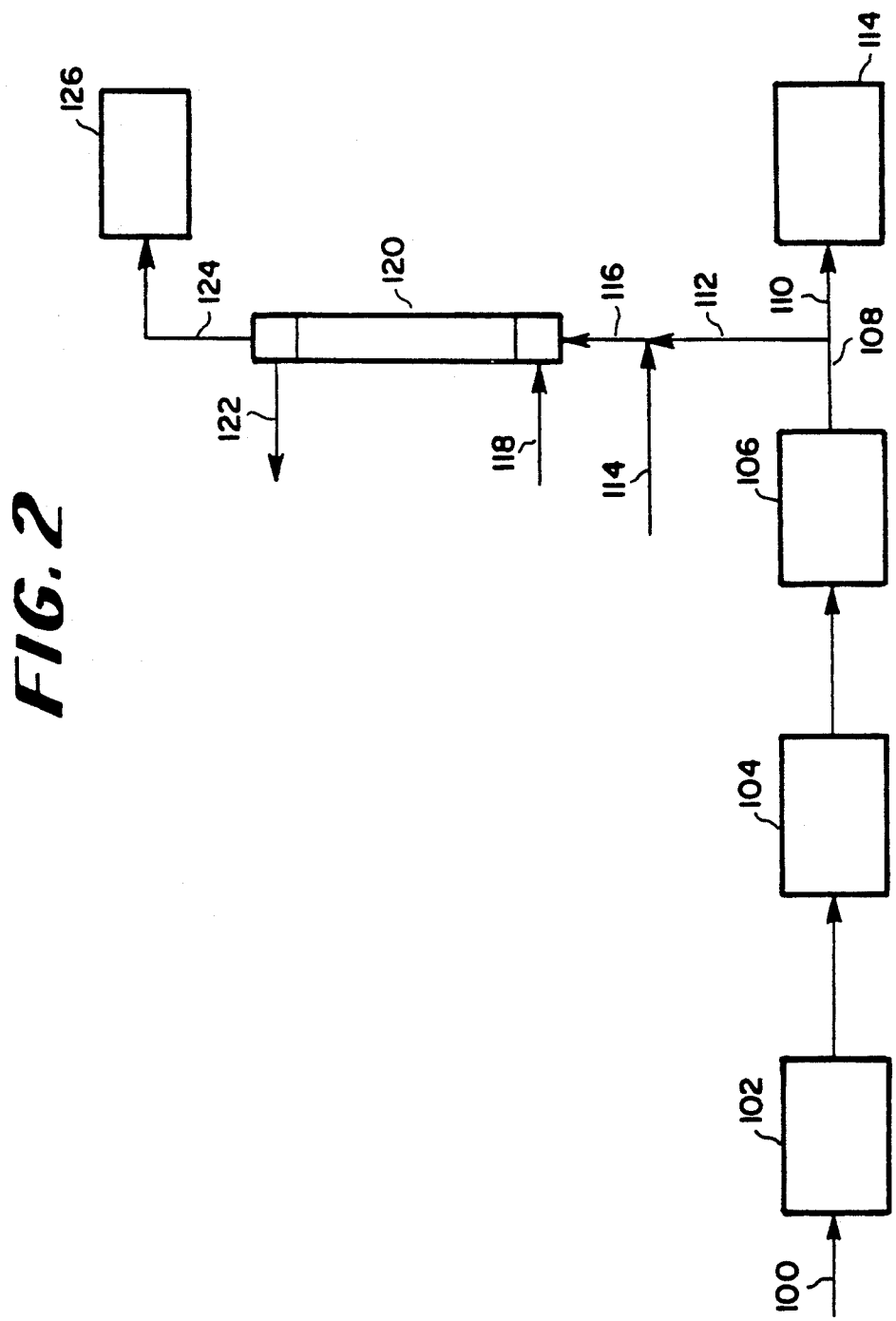

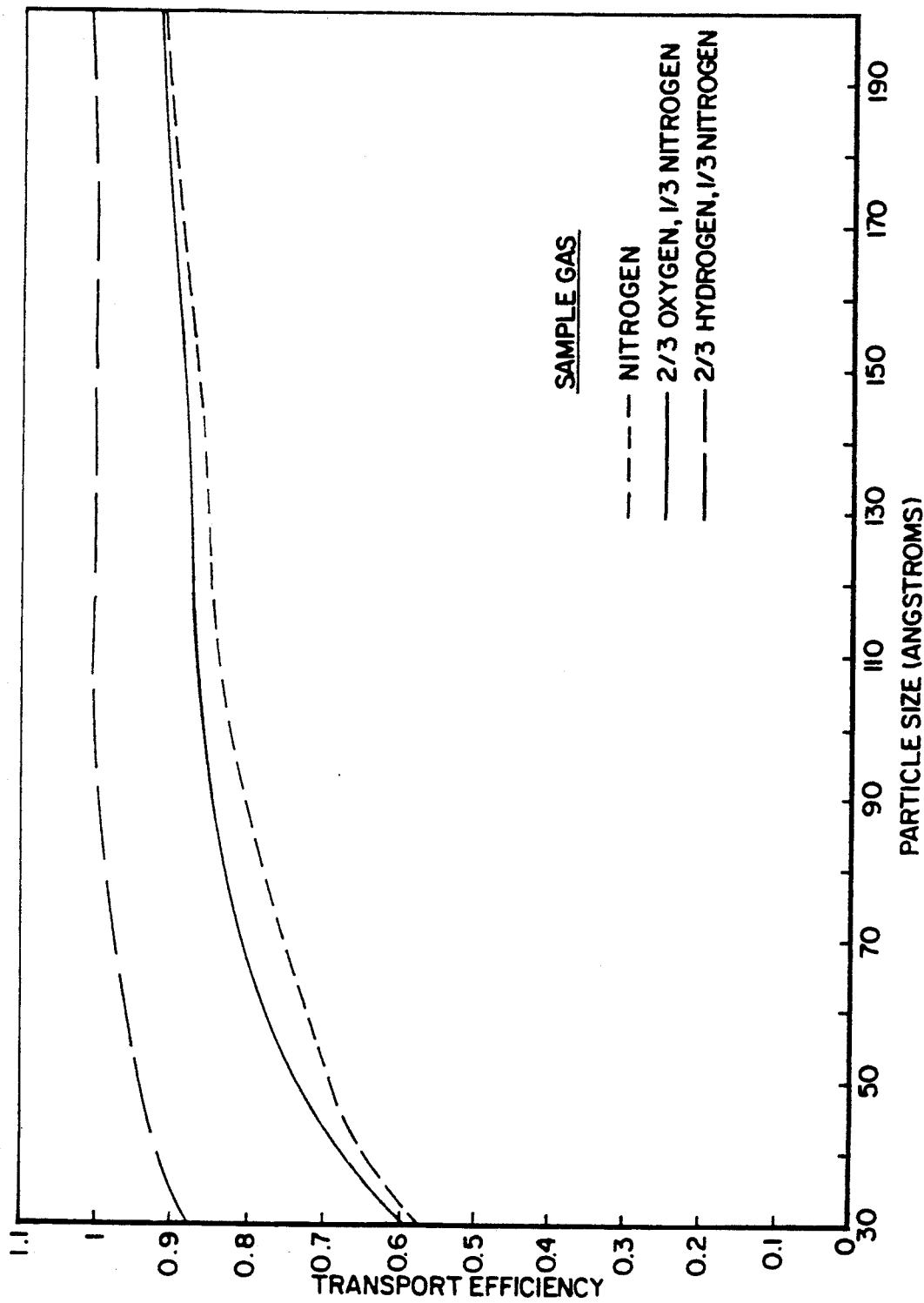

DIFFUSION GAS DILUTER

FIELD OF THE INVENTION

The present invention is directed to the field of diluting particle-containing fluids. More specifically, the present invention is directed to diluting particle-containing reactive fluids with a inert diluent fluid, while retaining the particle concentration for subsequent accurate counting in a nonreactive fluid media.

BACKGROUND OF THE PRIOR ART

Manufacturers of microelectronic devices require process gases having extremely low levels of entrained particulate contamination. Small quantities of microscopic contamination can damage micro circuits during the manufacturing process. Therefore, the concentration of contaminant particles in such gases must be tightly controlled. Modern filters are able to remove particulate contaminants in process gases with an extremely high efficiency. However, the complete assurance of contamination control also requires verification of gas cleanliness. An accurate technique for detecting microscopic particles in filtered gases must be available. Sensitive instruments capable of detecting particles as small as about 0.003 micrometer are readily available for inert process gases, such as nitrogen. However, particulate control must also be maintained in reactive gases, such as hydrogen and oxygen, which are used to manufacture various microcircuitries.

Instruments designed for inert gas particle counting cannot be used for 100% reactive gases, such as hydrogen or oxygen. Only a limited number of less sensitive instruments are available for hydrogen and oxygen type reactive gas particle counting service. Particles as small as about 0.1 micrometer can be measured in hydrogen or oxygen using, for example, certain particle counters manufactured by Particle Measuring Systems, Inc. of Boulder, Colo. These particle counters which belong to the family of so called laser spectrometers, have been especially designed for safety in the presence of 100% reactive sample gas streams and have been tested for proper calibration using these gases. However, there is presently no commercially available instrument to measure particles smaller than about 0.1 micrometer in oxygen or hydrogen.

Turbulent mixing diluters for diluting particulate containing reactive gases with inert diluent gases are known. However, various drawbacks in turbulent mixed diluters include the requirement for taking contamination measurements of both the dilution inert gas and the diluted particle-containing gas. In addition, microscopic particles which are of interest to the electronics industry are potentially lost on vessel walls in turbulent mixing diluters, which can throw off the detection of particles and thus make the measurement inaccurate. Such disadvantages for turbulent mixing vessels as diluters for reactive gas particle counting make them impractical for ultra clean low particle concentration gas applications requiring highly accurate measurements.

Other diluters are known in the industry such as set forth in U.S. Pat. No. 4,684,251 wherein a spectrometer with a sample diluter comprises a sample liquid line 19 which is diluted in vessel 1 with a diluent from vessel 10 which then flows in laminar flow through curved tubing 5 to an atomizer 6, after which the sample is burned and subject to spectrometric analysis. The curved nature of conduit 5 and the destruction of the sample after atomization makes this patent disclosing laminar flow inapplicable to enhancement of accurate particle counting.

U.S. Pat. No. 5,058,440 discloses a gas sampling dilution tunnel used for sampling the exhaust of an internal combustion engine particularly for particulates. A sampling probe 56 is introduced into a flow of particle-containing gas and removes a slip stream which is then mixed with diluent air introduced tangentially to the flow of the sample through a porous perforated tube 14 before being passed through a valve at a right angle where particles are adhered on filter 68. The tangential flow of diluent air with the concomitant addition of any particles in the diluent air to those in the sample gas and the angled flow path leading to a filter media, as well as retention of particles on the filter for counting makes this apparatus and procedure inappropriate for ultrafine, ultra low concentration particle detection in process gases used for the micro electronics industry.

U.S. Pat. No. 5,026,155 discloses a condensation nucleus counting device and method wherein a particle-containing gas in line 10 is contacted at capillary 22 with a working fluid vapor containing gas at a temperature such that the working fluid vapor condenses on the particles in conduit 26 and enlarged droplets surrounding the nucleating particles can be detected photometrically at the detection station 34 to provide an accurate count of particle contamination in the sampled gas stream. However, the working fluids are noted to be inclusive of alcohols and various organic materials which along with the materials of construction of the apparatus may be incompatible with various reactive gases, such as hydrogen and high purity oxygen.

The disadvantages of dilution and materials incompatibility of the prior art are overcome by the present invention, which is set forth in greater detail below.

BRIEF SUMMARY OF THE INVENTION

The present invention is an apparatus for diluting a particle-containing fluid with a diluent fluid to maintain the approximate number of particles of the particle-containing fluid in a resulting diluted particle-containing fluid, comprising: a laminar flow tube of a length sufficient to allow the dilution of the particle-containing fluid with the diluent fluid under conditions of coaxial laminar flow of the fluids longitudinally through the tube; a tubular injector situated coaxially inside a first end of the laminar flow tube and connected to a source of particle-containing fluid so as to inject a stream of particle-containing fluid into the laminar flow tube to flow longitudinally through the laminar flow tube from the first end to a second end; a tubular receiver situated coaxially inside the second end of the laminar flow tube for receiving the resulting diluted particle-containing fluid; an inlet plenum juxtaposed to the injector and closing the first end of the laminar flow tube which is connected to a supply of the diluent fluid to provide a coaxial sheath of diluent fluid around the particle-containing fluid from the injector; and an exit plenum chamber juxtaposed to the receiver and closing the second end of the laminar flow tube to remove effluent fluid from the laminar flow tube which forms the coaxial sheath around the diluted particle-containing fluid.

Preferably, the chamber is situated coaxially around the second end of the laminar flow tube and forms a flow channel which reverses the flow of the effluent fluid as it exits the laminar flow tube.

Preferably, the flow channel is formed between the chamber and an outer surface of the laminar flow tube.

More preferably, the chamber is connected to a vent for the effluent fluid.

Preferably, the inlet plenum has a sintered porous plate through which the diluent fluid passes before entering the laminar flow tube.

Preferably, the receiver is connected to a device to count the number of particles in the diluted particle-containing fluid. More preferably, the device is a condensation nucleus counter.

Preferably, the particle-containing fluid is a reactive gas and the diluent fluid is an inert gas. More preferably, the particle-containing fluid is selected from the group consisting of hydrogen and oxygen. Preferably, the diluent fluid is nitrogen.

Preferably, the reactive gas is diluted with the diluent gas in an amount sufficient to diminish the reactivity of the reactive gas.

The present invention is also a process for diluting a particle-containing fluid with a diluent fluid to maintain the approximate number of particles of the particle-containing fluid in a resulting diluted particle-containing fluid, comprising: introducing the particle-containing fluid through a tubular injector in an axial stream into a first end of a laminar flow tube of a length sufficient to allow the dilution of the particle-containing fluid with the diluent fluid under conditions of coaxial laminar flow of the fluids longitudinally through the tube; introducing the diluent fluid through an inlet plenum into the first end of the laminar flow tube to provide a coaxial sheath of diluent fluid around the particle-containing fluid from the injector; diffusing the fluids into one another to dilute the fluid of the particle-containing fluid with the diluent fluid while maintaining the particles in the axial stream; receiving the diluted particle-containing fluid in a tubular receiver situated coaxially inside a second end of the laminar flow tube; and removing effluent fluid from the laminar flow tube which forms the coaxial sheath around the diluted particle-containing fluid through an exit plenum chamber juxtaposed to the receiver at the second end of the laminar flow tube.

Preferably, the diluted particle-containing fluid is introduced into a particle counting device, to count the number of particles contained in the fluid. More preferably, the counting is by condensation nucleus counting in which the particles are contacted with a working fluid vapor, passed into a condensation zone where the vapor condenses on the particles as droplets and the droplets are counted by appropriate sensing and tabulation.

Preferably, the droplets are counted by a light scattering by the droplets.

Preferably, the reactive gas is diluted with the diluent gas in an amount sufficient to diminish the reactivity of the reactive gas with the working fluid vapor.

Preferably, the working fluid is selected in the group consisting of water, alcohols and perfluorinated organic compounds.

BRIEF DESCRIPTION OF THE DRAWINGS

FIG. 2 is a schematic illustration of the preferred embodiment of a diffusion diluter of the present invention used in conjunction with a particle counter and a source of particle-containing, fluid for testing the diffusion diluter.

FIG. 3 is a graph of particle transport efficiency for the apparatus and method of the present invention wherein transport efficiency is graphed against particle size in angstroms for test gases consisting of: nitrogen; two-thirds oxygen with one-third nitrogen; and two-thirds hydrogen with one-third nitrogen.

DETAILED DESCRIPTION OF THE INVENTION

Figure 1:
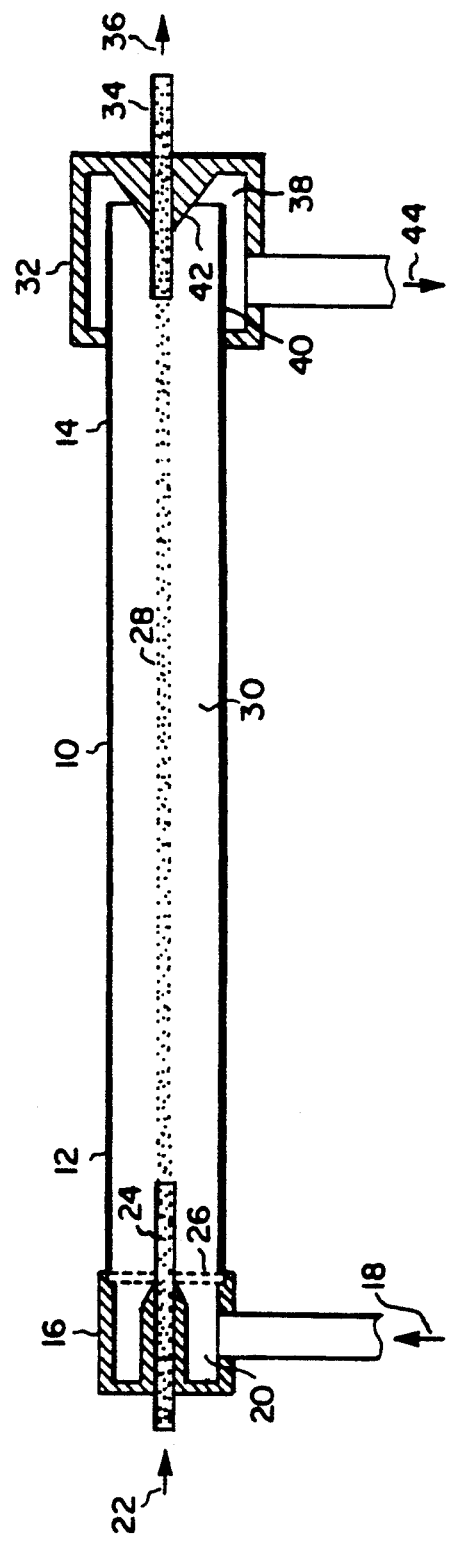
FIG. 1 is a side elevation in section of the preferred embodiment of the diffusion diluter of the present invention.

This invention provides a novel apparatus and process for diluting a particle-containing fluid stream in a second diluent fluid stream without simultaneously mixing their respective contained particle populations. The particle population of the first stream remains nearly intact. The resulting diluted fluid mixture can then be used for any subsequent purpose, such as contamination monitoring applications. In one application of this invention, the resulting diluted fluid stream is sent to a particle detecting instrument, which is compatible with and calibrated for the diluting fluid, such as nitrogen. This instrument is then used to directly measure the particle concentration of the original particle-containing fluid or gas.

This invention is suitable, for example, in measuring contaminant particles in ultra clean, reactive gases. The reactive gases may include either pure filtered hydrogen or pure filtered oxygen, as well as other reactive gases. However, the present invention could conceivably be applied to other gases considered incompatible with existing particle detecting instruments, which when diluted to sufficiently low levels in a second more compatible gas, could then be successfully introduced to the instruments for analysis. A particular advantage of the subject invention is that it does not turbulently mix the particle-containing fluid stream and the diluent fluid stream. The present invention utilizes a process of molecular diffusion to mingle the particle-containing reactive fluid or gas with the diluent fluid or gas. By using this molecular diffusion technique, the desired dilution is accomplished without substantially changing the particle concentration of the particle-containing fluid or gas.

A preferred embodiment of the present invention apparatus is shown in FIG. 1. Typically, the flow rate of the inner or core particle-containing reactive fluid could be 1.4 liters per minute. This flow rate accommodates the requirements of existing inert gas condensation nucleus counters, which would be downstream of the apparatus of FIG 1. Such condensation nucleus counters could include 0.02 micrometer (200 angstrom) instruments and 0.003 micrometer (30 angstrom) instruments. The diffusion diluter apparatus of the present invention can be used with reactive gases, such as hydrogen or oxygen. The dimensions of the diffusion diluter are such to provide sufficient dilution of such gases interchangeably without changes in operating conditions.

One of the more extreme dilution rates (to 7%) is required for reactive gases, such as hydrogen. However, since the molecular diffusion proceeds gradually along the diffusion diluter apparatus, less than complete dilution can be expected in a finite length laminar flow tube where diffusion occurs. Therefore, the flow rate of the outer or sheath fluid stream used as a diluent can be set to approximately 46 liters per minute in the disclosed embodiment. Such a flow ratio would provide a completely diluted concentration of approximately 3%. Accordingly, the required 7% axial dilution for a reactive gas, such as hydrogen, can be achieved in a tube of reasonable length. The diameter of the laminar flow tube of the diffusion diluter apparatus can be sized to provide a relatively low average flow velocity typically of 31 centimeters per second using a 5.7 centimeter diameter tube. This would ensure that the Reynolds number of the gases is low enough to provide laminar flow. A sintered porous metal plate or other appropriate flow straightening device can be located near the entrance of the diluent fluid stream. This plate serves to reduce turbulence in the incoming diluent fluid stream and can create a relatively uniform inlet flow of such gas. The inlet plenum for the sheath diluent fluid can be filled with glass wool or other appropriate dense medium to provide additional flow resistance for increased inlet flow uniformity. Since condensation nucleus counters are designed to receive gas samples at standard temperature and pressure, the diffusion diluter can be operated at about 1 atmosphere and 21° C.

With reference to FIG. 1, the diffusion diluter apparatus comprises a laminar flow tube 10 having a first end 12 and second end 14. An inlet plenum 16 is affixed at the first end 12 of the laminar flow tube 10. A tubular injector 24 passes coaxially through the inlet plenum 16 to deliver a particle-containing reactive gas 22 through the injector 24 into the inside 30 of the tube 10. This particle-containing reactive gas is diluted with an inert diluent gas 18 supplied in a line entering into the coaxial plenum chamber 20 of the inlet plenum 16. This inert diluent gas passes through a sintered porous metal plate 26 to diminish flow currents and to preserve an entirely laminar flow of the particle-containing reactive gas passing coaxially centrally through the tube 10 in a longitudinal flow path 28 which is surrounded by a coaxial laminar and sheath like flow of diluent gas between the tube wall 10 and the particle-containing axial flow stream 28.

As the particle-containing fluid 28 and the diluent fluid pass longitudinally through the tube 10, from its first end 12 to its second end 14, the particles, which are heavier, remain in their flowpath, whereas the molecules of the respective fluids or gases diffuse readily, due to their lighter weight, so that at the second end 14 of the tube 10, the particles remain in their orientation coming out of the injector 24, whereas the reactive gas has diffused into the diluent gas to result in a resulting particle-containing diluted gas or fluid, which is received by the tubular receiver 34 coaxially aligned in the second end 14 of the tube 10. This gas or fluid, containing essentially all the particles of the gas 22, is removed as a stream in line 36, typically to be counted in a condensation nucleus counter device. That fluid or gas which is not commingled with the particles is removed in an exit plenum chamber 32, which typically is coaxially aligned with the second end 14 of the tube and spaced from the end of the tube so as to allow a flowpath of the effluent fluid out of the tube without interference with the flow of particles 28 through the tube 10. The effluent gas 44 passes through a channel 38 formed by the chamber 32 and the external wall 40 of the second end 14 of the tube 10 before exiting as a vent 44 in a line emanating from the chamber 32.

In a preferred example of the present invention, the diameter (0.98 centimeter) of the coaxially centrally located tubular injector 24 was sized to approximately match the average velocity of the particle-containing fluid stream with the average velocity of the diluent or sheath fluid stream. Any substantial disparity in flow velocities between the two fluid streams would tend to produce fluid shear layers resulting in free stream turbulence. The diameter (0.98 centimeter) and draw off rate (1.4 liters per minute) of the coaxially centrally located tubular receiver 34 were set to match those of the injector. Preferably, the ends of the injector and receiver are sharply tapered in order to minimize flow disturbances that could be generated by blunt tube ends. The used diluent or effluent gas which constitutes the sheath gas is drawn off in the exit plenum chamber 32 in a symmetric flow pattern. Multiple symmetric sources of venting of the exit plenum chamber 32 are desirable in order to preserve the coaxial laminar flow paths of the diluent and particle-containing fluid or gas streams. Any deviation in the coaxial laminar flow paths would prevent complete capture of the particle-containing fluid 28 by the receiver 34. The exit plenum chamber 32 is designed to minimize the disturbing influence of downstream vent means on the internal flow patterns within the laminar flow tube 10. The effluent fluid gas stream in the exit plenum chamber 32 first flows past the tubular receiver 34 and then diverges radially outward against a flow surface 42 in the exit plenum chamber 32. The effluent fluid stream then reverses direction in the exit plenum chamber 32 before flowing into symmetrically oriented side mounted vent outlets. The pressure drop associated with the flow reversal tends to isolate the laminar flow tube's internal flow patterns from any disturbances created by the downstream vent outlets.

In a preferred example of the present invention, the length (41 centimeters) of the laminar flow diffusing zone between the tubular injector 24 and the receiver 34 was sized to provide 7% axial dilution for an easily diffusing reactive gas, such as hydrogen, and 17% axial dilution for a less easily diffusing reactive gas, such as oxygen.

For some light reactive gases which constitute the particle-containing fluid treated by the present invention, it may be desirable to position the laminar flow tube in a vertical orientation so that buoyancy effects of potentially lighter molecules of a reactive gas, such as hydrogen, would not come into play when contacted with a heavier molecule containing diluent gas, such as nitrogen. For other gases, which have more closely matched molecular weights, such as mixtures of an oxygen particle-containing reactive gas and a nitrogen diluent gas, orientation of the laminar flow tube to avoid buoyancy factors may not be required.

It is necessary that particles be transported efficiently through the diffusion diluter and that their concentration remain nearly unchanged during the dilution process in order for the apparatus and process of the present invention to provide an accurate measurement of the particle content of the reactive gas or fluid. Tests were performed to determine the efficiency of particle transport through the diffusion diluter of the present invention. The tests were performed using particle-containing reactive gas streams. The efficiency of particle transport through the diffusion diluter should depend upon the particle size. This is because smaller particles are more mobile and therefore more strongly affected by Brownian motion and diffusion. Small particles therefore have a greater tendency to deviate in their paths from the fluid stream lines. This deviation tends to reduce their chance of being captured by the receiver. The smaller the particle or the longer the tube the greater this effect becomes. The reactive sample gases of the present experiment were seeded with test particles of a known single size. These particle-containing reactive gas streams were produced by preparing a solution of sodium chloride in electronics grade water. Nitrogen was used to atomize the suspension, thereby producing a fine salt water mist.

With reference to FIG. 2, this verification experiment of the apparatus and process of the present invention will be illustrated. The filtered, particle-free nitrogen in line 100 was passed through an atomizer 102 where it contacted a fine salt water mist. The resulting water droplets quickly evaporated leaving sodium chloride particles suspended in a mixture of nitrogen and water vapor. The water vapor was then removed by flowing the aerosol through a diffusion-type drier 104. The result was a dry nitrogen stream containing suspended sodium chloride particles and numerous non-volatile residue particles of various sizes. The resulting sodium chloride particles also had various sizes, generally larger than 0.01 micrometer, but in some cases smaller than 0.01 micrometer.

The formed aerosol was then passed through a size selecting apparatus designed to reject all but one size particle. This apparatus, referred to as a differential mobility analyzer 106, was set to select only the desired size particles, rejecting all others. The result was a filtered, particle-free nitrogen stream containing a highly monodisperse (single size) suspension of sodium chloride particles. The concentration of particles in this aerosol was then directly measured using an inert gas particle detector being fed the sodium chloride particle-containing gas from line 108 through inlet 110 into the detector 114. The stream in line 108 was partially diverted into line 112 and diluted with a highly filtered reactive gas stream, comprising hydrogen or oxygen from line 114, in such a proportion that the resulting mixture contained approximately two-thirds reactive gas and approximately one-third nitrogen. The result was a predominately reactive gas mixture containing a known concentration of single-size particles in line 116.

In some cases for this experiment, the particle-containing nitrogen was not merged with reactive gas, but was used alone as a sample gas. In this way three different gas mixtures were used as sample streams. This permitted an evaluation of the effect of sample stream composition on particle transport efficiency.

These sample gases were then introduced into the diffusion diluter apparatus 120 of the present invention using a diluent gas as a sheath gas introduced in 118 with the effluent gas removed in line 122. The sheath or diluent nitrogen gas stream was highly filtered and contained a negligible concentration of particles. The concentration of particles in the resulting diluted particle-containing gas stream 124 was then measured using an identical inert gas particle detector 126 to the detector 114. The concentration of particles measured in detector 126 was compared to the known concentration of particles in the diffusion diluter feedstream of line 116. The ratio of the measured concentration of particles in the diluted particle-containing gas stream 124 to the known concentration of particles in the diffusion diluter feed stream 116 was defined as the particle transport efficiency. The test was repeated for various particle sizes and the results are shown in FIG. 3.

The data in FIG. 3 show that particle transport efficiency through the diffusion diluter apparatus of the present invention is size dependent as would be expected. Transport efficiency declines as particle size is decreased and particle diffusion becomes more important. The data suggest that the particle transport efficiency is higher when hydrogen/nitrogen is used as a sample gas. When the sample gas is oxygen/nitrogen or nitrogen, the efficiency falls to about 65% at 40 angstroms particle size. Above 100 angstroms particle size, the efficiency approaches 100% for all sample gases. This performance provides a highly viable apparatus and technique for the accurate monitoring of filtered process gases, such as those used in the semiconductor fabrication industry.

The present invention provides a superior apparatus and method for mingling a reactive gas and an inert gas to produce an essentially inert resulting gas without substantially commingling any existing entrained particle populations in the two gas streams. This is accomplished through the process of molecular diffusion. A concentration gradient between the reactive gas and the diluent gas provides a driving force for molecular diffusion. Each gas therefore diffuses into the other. This diffusion tends toward a condition of uniform composition. This process of diffusion is described by the well known Fick's first law of diffusion. This law states that a single component of a gas mixture will diffuse through the mixture at a rate which is proportional to the concentration gradient of that component. The constant of proportionality is given by the mass diffusion coefficient for the two gases.

The rate at which particles diffuse through gases is in many cases lower than for gas molecules. Particles tend to diffuse through gases in a manner analogous to molecular diffusion. This Brownian diffusion of particles becomes greater as particle size is decreased. This is because smaller particles have higher mobilities tending to approach those of molecules. However, even particles as small as 20 angstroms have diffusion coefficients approximately an order of magnitude smaller than those of typical low molecular weight gases of interest, as illustrated below.

Mass Diffusivity: Hydrogen in Nitrogen = 0.674 $cm^2/sec$

Mass Diffusivity: Oxygen in Nitrogen = 0.181 $cm^2/sec$

Diffusion Coefficient: 0.002 micrometer (20 angstroms) particles in air = approximately 0.015 $cm^2/sec$ A comparison of the above values demonstrates that even particles as small as 20 angstroms are much less mobile than diffusing molecules. Particles larger than 20 angstroms are even less mobile and therefore less likely to diffuse away from the center line prescribed by the tubular injector and tubular receiver of the apparatus of the present invention. Therefore, all particles of interest can be considered to nearly follow the flow stream lines during the dilution process of the present invention.

The above analysis suggests that no significant loss of sample stream particles will occur during the dilution process of the present invention. By the same reasoning, it can be expected that no significant addition of new particles to the sample stream should occur through the diffusion from the surrounding diluent or sheath gas. Therefore, the measured particle concentration of the sample stream can be considered to be relatively unaffected by the particle concentration in the incoming diluent gas. Consequently, it is not necessary to separately measure the contamination level of the diluent gas.

In summary, the diffusion diluter apparatus and process of the present invention provides means for creating nonturbulent contact between two flowing streams of separate gases or fluids, one being the particle-containing sample gas or fluid, the other being a diluent gas or fluid. When two separate gases or fluids are brought into contact, and when no turbulence is present, then diffusion becomes the dominant mechanism for molecular and particle interchange between the two gases or fluids. The two gases or fluids move co-currently through a laminar flow tube in such a manner that a strong concentration gradient is initially established between the two gases or fluids leading to molecular diffusion. This molecular diffusion tends toward a condition of compositional uniformity among the two gases or fluids. The time of contact between the two gases or fluids, as determined by the residence time within the laminar flow tube, is set such that the desired degree of molecular diffusion is accomplished such as to render a reactive gas essentially non-reactive, without causing a substantial amount of particle interchange between the two gases or fluids through Brownian diffusion. The result is that a substantial change in the particle containing sample gas composition is effected, such as to render it essentially non-reactive for particle counting purposes without causing a substantial change in the particle content of the particle-containing sample gas or fluid stream. This provides a method for the direct measurement of particles in gas or fluid streams, which are reactive in nature, using available inert gas particle detectors, such as condensation nucleus counters as described in U.S. Pat. No. 5,026,155, which is hereby incorporated herein in its entirety by reference. Such condensation nucleus counters are typically used to detect small particles in gases for ultra high purity gas cleanliness analysis, such gases to be used, for example, in microelectronics fabrication. Condensation nucleus counting comprises passing a particle-containing gas mixed with a working fluid vapor into a condensation zone, condensing working fluid on the particles to form droplets which enlarge the overall size of the particles that they surround, making it feasible to detect these particles by the enlarged droplet surrounding the particle and detecting the resulting droplets and counting the number of droplets by the use of light diffraction in a photometric cell, which provides an electronic signal responsive to the number of particles based upon the droplet condensation on such particles.

The diffusion diluter of the present invention would be used immediately upstream of such a condensation nucleus counting device to render potentially reactive particle-containing gases, such as hydrogen or oxygen, non-reactive by diffusion with an inert gas, without diminishing their particle concentration, wherein the diluted reactive gas would then be compatible with materials of construction of the condensation nucleus counter and their working fluid vapors, which typically comprise alcohol, such as butanol, to result in a safe and accurate counting of submicrometer particles in otherwise reactive gas streams.

The present invention has been described with reference to a single preferred embodiment, however, the full scope of the present invention should be ascertained from the claims which follow.

We claim:

1. An apparatus for diluting a particulate-containing fluid with a diluent fluid to maintain the approximate number of particles of the particle-containing fluid in a resulting diluted particles-containing fluid, comprising:

(a) a laminar flow tube of a length sufficient to allow the dilution of said particle-containing fluid with said diluent fluid under conditions of coaxial laminar flow of said fluids longitudinally through said tube while maintaining the approximate number of particles of said particle-containing fluid in said resulting diluted particle-containing fluid;

(b) a tubular injector situated coaxially inside a first end of said laminar flow tube and connected to a source of particle-containing fluid so as to inject a stream of particle-containing fluid into said laminar flow tube to flow longitudinally through said laminar flow tube from said first end to a second end;

(c) a tubular receiver situated coaxially inside said second end of said laminar flow tube for receiving said resulting diluted particle-containing fluid;

(d) an inlet plenum juxtaposed to said injector and closing said first end of said laminar flow tube which is connected to a supply of said diluent fluid to provide a coaxial sheath of diluent fluid around the particle-containing fluid from said injector; and (e) an exit plenum chamber juxtaposed to said receiver and closing said second end of said laminar flow tube to remove effluent fluid from said laminar flow tube which forms the coaxial sheath around said diluted particle-containing fluid.

2. The apparatus of claim 1 wherein said chamber is situated coaxially around said second end of said laminar flow tube and forms a flow channel which reverses the flow of said effluent fluid as it exits said laminar flow tube.

3. The apparatus of claim 2 wherein said flow channel is formed between said chamber and an outer surface of said laminar flow tube.

4. The apparatus of claim 1 wherein said chamber is connected to a vent for said effluent fluid.

5. The apparatus of claim 1 wherein said inlet plenum has a sintered porous plate through which said diluent fluid passes before entering said laminar flow tube.

6. The apparatus of claim 1 wherein said receiver is connected to a device to count the number of particles in said diluted particle-containing fluid.

7. The apparatus of claim 6 wherein said device is a condensation nucleus counter.

8. The apparatus of claim 7 wherein said particle-containing fluid is a reactive gas and said diluent fluid is an inert gas.

9. The apparatus of claim 1 wherein said particle-containing fluid is selected from the group consisting of hydrogen and oxygen.

10. The apparatus of claim 1 wherein said diluent fluid is nitrogen.

11. The apparatus of claim 8 wherein said reactive gas is diluted with said inert gas in an amount sufficient to diminish the reactivity of said reactive gas with a working fluid vapor of said condensation nucleus counter.

12. A process for diluting a particle-containing fluid with a diluent fluid to maintain the approximate number of particles of the particle-containing fluid in a resulting diluted particle-containing fluid, comprising:

(a) introducing said particle-containing fluid through a tubular injector in an axial stream into a first end of a laminar flow tube of a length sufficient to allow the dilution of said particle-containing fluid with said diluent fluid under conditions of coaxial laminar flow of said fluids longitudinally through said tube while maintaining the approximate number of particles of said particle-containing fluid in said resulting diluted particle-containing fluid;

(b) introducing said diluent fluid through an inlet plenum into said first end of said laminar flow tube to provide a coaxial sheath of diluent fluid around said particle-containing fluid from said injector;

(c) diffusing said fluids into one another to dilute the fluid of said particle-containing fluid with said diluent fluid while maintaining said particles in said axial stream;

(d) receiving said diluted particle-containing fluid in a tubular receiver situated coaxially inside a second end of said laminar flow tube; and (e) removing effluent fluid from said laminar flow tube which forms the coaxial sheath around said diluted particle-containing fluid through an exit plenum chamber juxtaposed to said receiver at said second end of said laminar flow tube.

13. The process of claim 12 wherein said diluted particle-containing fluid is introduced into a particle counting device to count the number of particles contained in said fluid.

14. The process of claim 13 wherein the counting is by condensation nucleus counting in which said particles are contacted with a working fluid vapor, passed into a condensation zone where said vapor condenses on said particles as droplets and said droplets are counted by appropriate sensing and tabulation.

15. The process of claim 14 wherein said droplets are counted by light scattering by said droplets.

16. The process of claim 14 wherein said particle-containing fluid is a reactive gas and said diluent fluid is an inert gas.

17. The process of claim 16 wherein said reactive gas is diluted with said diluent gas in an amount sufficient to diminish the reactivity of said reactive gas with said working fluid vapor.

18. The process of claim 14 wherein said working fluid vapor is selected from the group consisting of water, alcohols and perfluorinated organic compounds.

19. The process of claim 12 wherein said particle-containing fluid is selected from the group consisting of hydrogen and oxygen.

20. The process of claim 12 wherein said diluent fluid is nitrogen.

21. An apparatus for diluting a particular-containing reactive gas with an inert diluent gas to maintain the approximate number of particles of the particle-containing gas in a resulting diluted particle-containing gas, comprising:

(a) a laminar flow tube of a length sufficient to allow the dilution of said particle-containing reactive gas with said inert diluent gas under conditions of coaxial laminar flow of said gases longitudinally through said tube;

(b) a tubular injector situated coaxially inside a first end of said laminar flow tube and connected to a source of particle-containing reactive gas so as to inject a stream of particle-containing reactive gas into said laminar flow tube to flow longitudinally through said laminar flow tube from said first end to a second end;

(c) a tubular receiver situated coaxially inside said second end of said laminar flow tube for receiving said resulting diluted particle-containing gas;

(d) an inlet plenum juxtaposed to said injector and closing said first end of said laminar flow tube which is connected to a supply of said inert diluent gas to provide a coaxial sheath of inert diluent gas around said particle-containing reactive gas from said injector;

(e) an exit plenum chamber juxtaposed to said receiver and closing said second end of said laminar flow tube to remove effluent gas from said laminar flow tube which forms the coaxial sheath around said diluted particle-containing gas; and (f) a condensation nucleus counter connected to said receiver to count the number of particles in said diluted particle-containing gas using a working fluid, wherein said particle-containing reactive gas is diluted with said inert diluent gas in an amount sufficient to diminish the reactivity of said particle-containing reactive gas with said working fluid.

22. A process for diluting a reactive particle-containing gas with an inert diluent gas to maintain the approximate number of particles of said reactive particle-containing gas in a resulting diluted particle-containing gas, comprising:

(a) introducing said particle-containing gas through a tubular injector in an axial stream into a first end of a laminar flow tube of a length sufficient to allow the dilution of said reactive particle-containing gas with said inert diluent gas under conditions of coaxial laminar flow of said gases longitudinally through said tube;

(b) introducing said inert diluent gas through an inlet plenum into said first end of said laminar flow tube to provide a coaxial sheath of inert diluent gas around said reactive particle-containing gas from said injector;

(c) diffusing said gases into one another to dilute the gas of said reactive particle-containing gas with said inert diluent gas while maintaining said particles in said axial stream;

(d) receiving said diluted particle-containing gas in a tubular receiver situated coaxially inside a second end of said laminar flow tube;

(e) removing effluent gas from said laminar flow tube which forms the coaxial sheath around said diluted particle-containing gas through an exit plenum chamber juxtaposed to said receiver at said second end of said laminar flow tube; and (f) counting the number of particles contained in said diluted particle-containing gas in a condensation nucleus counter in which said particles are contacted with a working fluid vapor, passed into a condensation zone where said vapor condenses on said particles as droplets and said droplets are counted by appropriate sensing and tabulation, wherein said reactive particle-containing gas is diluted with said inert diluent gas in an amount sufficient to diminish the reactivity of said reactive gas with said working fluid vapor.

* * * * *